United States Patent
Hadas

(10) Patent No.: US 10,219,935 B2
(45) Date of Patent: Mar. 5, 2019

(54) INTRA-ORAL DEVICE FOR UPPER AIRWAY SUPPORT

(71) Applicant: THOMAS MEDICAL LTD., Tel Aviv (IL)

(72) Inventor: Noam Hadas, Tel Aviv (IL)

(73) Assignee: THOMAS MEDICAL LTD., Tel Aviv (IL)

(*) Notice: Subject to any disclaimer, the term of this patent is extended or adjusted under 35 U.S.C. 154(b) by 0 days.

(21) Appl. No.: 15/562,419

(22) PCT Filed: Mar. 27, 2016

(86) PCT No.: PCT/IL2016/050327
§ 371 (c)(1),
(2) Date: Sep. 28, 2017

(87) PCT Pub. No.: WO2016/157174
PCT Pub. Date: Oct. 6, 2016

(65) Prior Publication Data
US 2018/0125701 A1 May 10, 2018

Related U.S. Application Data

(60) Provisional application No. 62/141,289, filed on Apr. 1, 2015.

(51) Int. Cl.
*A61F 5/56* (2006.01)
*A61C 7/36* (2006.01)
*A61B 5/00* (2006.01)

(52) U.S. Cl.
CPC ............ *A61F 5/566* (2013.01); *A61B 5/4818* (2013.01); *A61C 7/36* (2013.01); *A61B 5/4815* (2013.01)

(58) Field of Classification Search
CPC ........ A61C 7/36; A61B 5/4818; A61B 5/4815
See application file for complete search history.

(56) References Cited

U.S. PATENT DOCUMENTS 4,669,459 A * 6/1987 Spiewak ................. A61F 5/566
128/848
5,915,385 A 6/1999 Hakimi
(Continued)

FOREIGN PATENT DOCUMENTS

JP 2013106811 6/2013
WO 2010096573 8/2010

*Primary Examiner* — Timothy Stanis
(74) *Attorney, Agent, or Firm* — Mark M. Friedman

(57) ABSTRACT

A device reduces breathing obstructions of a user. A base member removably couples to the upper or lower jaw of the user. An elastic support member couples to the base member and includes at least one contact surface for contacting at least one region of tissue. The elastic support member moves between a retracted state and a deployed state. In the retracted state, the at least one contact surface spatially separates from the at least one region of tissue. In the deployed state, at least a portion of the elastic support member extends such that the at least one contact surface contacts the at least one region of tissue preventing at least partial collapse of at least a section of the upper airway. A control unit actuates an electro-mechanical drive arrangement to move the elastic support member between the retracted and deployed states.

19 Claims, 8 Drawing Sheets

(56) References Cited

U.S. PATENT DOCUMENTS

| | | | |
|---|---|---|---|
| 6,453,905 B1 * | 9/2002 | Conrad | A61F 5/566 |
| | | | 128/898 |
| 7,882,842 B2 | 2/2011 | Bhat | |
| 8,857,439 B2 | 10/2014 | Hegde | |
| 2004/0045555 A1 * | 3/2004 | Nelson | A61F 5/566 |
| | | | 128/848 |
| 2010/3019710 | 12/2010 | Sharkawy | |
| 2011/0178439 A1 | 7/2011 | Irwin et al. | |
| 2011/0226264 A1 | 9/2011 | Friedman et al. | |
| 2011/0315149 A1 * | 12/2011 | Tielemans | A61F 5/566 |
| | | | 128/848 |
| 2014/0135868 A1 | 5/2014 | Bashyam | |
| 2016/0022473 A1 | 1/2016 | Winters | |

\* cited by examiner

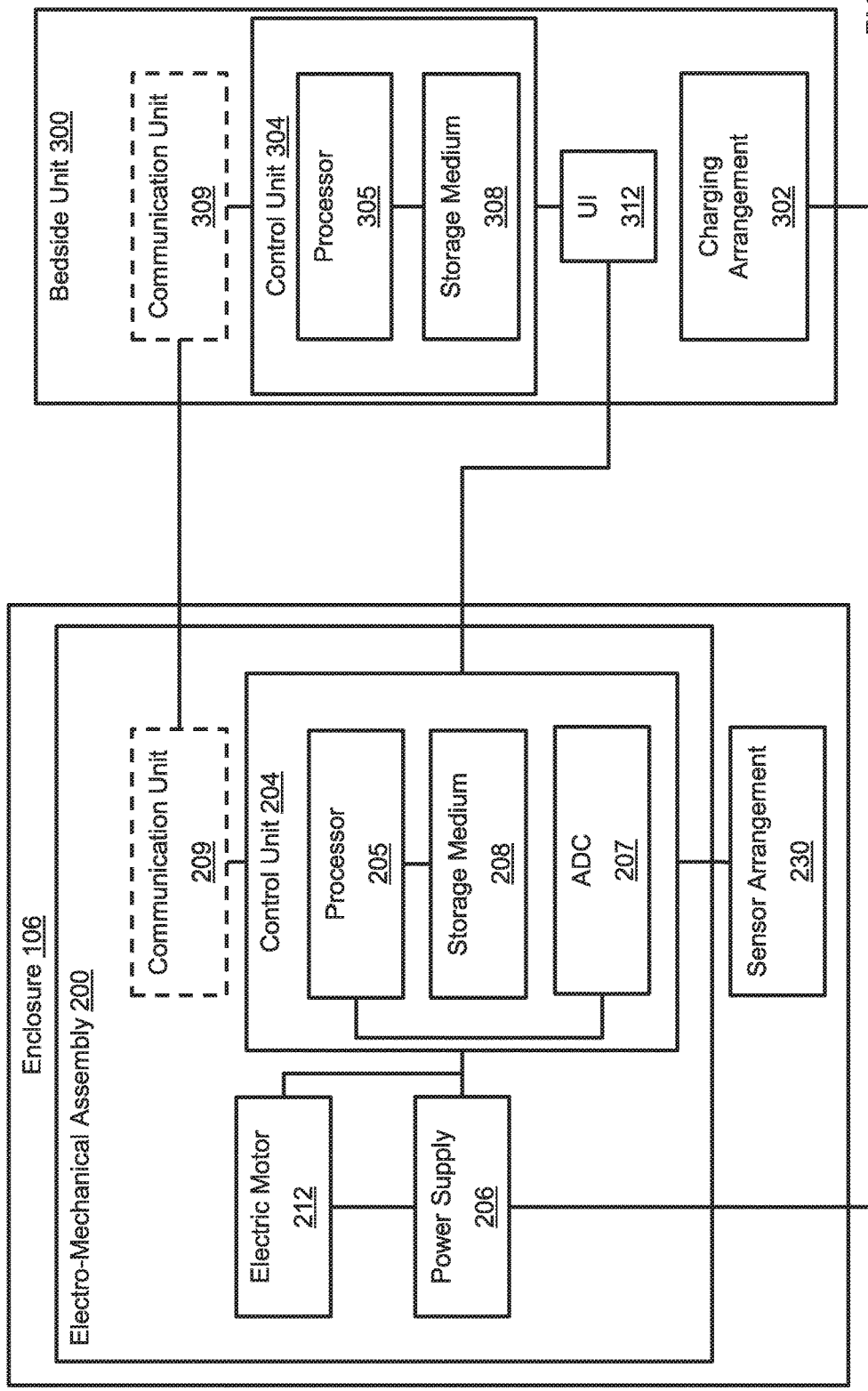

INTRA-ORAL DEVICE FOR UPPER AIRWAY SUPPORT

CROSS-REFERENCE TO RELATED APPLICATIONS

This application claims priority from U.S. Provisional Patent Application No. 62/141,289, filed Apr. 1, 2015, whose disclosure is incorporated by reference in its entirety herein.

TECHNICAL FIELD

The present invention relates to upper airway supportive medical devices.

BACKGROUND OF THE INVENTION

Sleep disorders which affect breathing are characterized by repetitive episodes of reduced breathing during sleep. Obstructive Sleep Apnea (OSA), for example, results in episodes of intermittent cessation of airflow, with each episode typically lasting 10 seconds or more. These interruptions in airflow occur when the tongue and other soft tissue of the nasopharynx and oropharynx are affected by the flow of air through the upper airway, as well as by the low pressure generated by the respiratory effort of the patient. In patients with OSA, such effects are relatively large, and result in a partial or complete blockage of the flow of air through the upper airway. These blockages lead to a drop in oxygen supply to the blood, which eventually wakes the patient, after which normal respiration is resumed. Typically, once the patient falls back asleep, the process of airway blockages and waking repeats. Such repetition often continues periodically throughout sleep, in some cases averaging 60 or more episodes per hour of sleep, having consequentially devastating effects on the health and well-being of the patient.

One family of techniques developed to treat sleep apnea uses compressors and facial masks to maintain patient respiratory pressure support with continuous positive airway pressure (CPAP) during sleep. Such techniques are typically implemented with devices known as CPAP machines. Although CPAP machines are highly effective in treating sleep apnea, they are cumbersome to the patient, requiring the patient to wear the CPAP machine mask throughout sleep. Furthermore, patient mobility during sleep is limited by a hose which connects the CPAP mask to the compressor. Additionally, the positive air pressure in the upper airways is very uncomfortable, and often leads to flu-like and other side effects.

Alternative techniques are currently in development, which rely on devices that are surgically implanted in tissue in the mouth of the patient to reduce the effects that cause apnea episodes. However, these techniques are far from being commercial and may pose hygienic liabilities. Non-surgical techniques rely on inserting mouth pieces which move the lower jaw forward thus opening an airway behind the tongue, but these devices are not very effective. Other intra-oral devices, having permanently deployed stents or tongue retaining protrusions for reducing upper airway obstructions have been tried, but failed commercially, because such stents have negative physiological effects on the patient, as insertion of a deployed stent into the mouth stimulates the gag reflex and causes general discomfort. Such negative physiological effects can also devolve into negative psychological effects, as patients become wary of inserting devices into the mouth which will trigger the gag reflex.

SUMMARY OF THE INVENTION

The present invention is an intra-oral device for providing upper airway support to reduce breathing obstructions.

According to the teachings of an embodiment of the present invention, there is provided a device for reducing breathing obstructions of a user, the device comprising: a base member for removably coupling to the upper or lower jaw of the user; an elastic support member operatively coupled to the base member, the elastic support member including at least one contact surface for contacting at least one region of tissue, the elastic support member movable between a retracted state, in which the at least one contact surface is spatially separated from the at least one region of tissue, and a deployed state, in which at least a portion of the elastic support member is extended, such that the at least one contact surface contacts the at least one region of tissue to prevent at least partial collapse of at least a section of the upper airway; an electro-mechanical drive arrangement in mechanical driving relationship with the elastic support member; and a control unit associated with the electro-mechanical drive arrangement, the control unit configured for actuating the electro-mechanical drive arrangement to move the elastic support member between the retracted and deployed states.

Optionally, when the elastic support member is in the retracted state, the elastic support member assumes an initial volume, and when the elastic support member is in the deployed state, the elastic support member is operative to assume a range of volumes between an initial deployed volume and a maximum deployed volume, the initial volume being approximately less than 10% of the maximum deployed volume.

Optionally, when the elastic support member is in the retracted state, the elastic support member assumes an initial length, and when the elastic support member is in the deployed state, the elastic support member is operative to assume a range of lengths between an initial deployed length and a maximum deployed length.

Optionally, when the elastic support member is in the retracted state, substantially the majority of the elastic support member is retained in a compressed state within the mouth of the user.

Optionally, the rate of movement of at least the portion of the elastic support member during movement from the retracted state to the deployed state is in the range of 0.5-20 millimeters per minute.

Optionally, movement between the retracted state to the deployed state is induced by rotation of the elastic support member about the longitudinal axis of the elastic support member.

Optionally, the elastic support member includes a helical spring.

Optionally, the helical spring includes a plurality of coils, and the spacing between each coil is in the range of 4-15 millimeters.

Optionally, the helical spring has a cross-sectional diameter, in a plane perpendicular to the longitudinal axis of the helical spring, in the range of 5-20 millimeters.

Optionally, the elastic support member further includes a coating of low friction material for coating the helical spring.

Optionally, the coating has a thickness in the range of 50-300 microns.

Optionally, the at least one region of tissue includes a plurality of regions of tissue, and subsequent to movement of the elastic support member to the deployed state, the elastic support member is operative to maintain continuous movement to reposition the at least one contact surface to contact any of the plurality of regions of tissue.

Optionally, the continuous movement is induced by a rotation about the longitudinal axis of the elastic support member at a rate in the range of 0.1-1 rotations per minute.

Optionally, the electro-mechanical drive arrangement includes a cylinder arrangement comprising an inner cylinder including an exterior surface, and a hollow outer cylinder including an interior surface defining an interior volume, at least a portion of the inner cylinder being positioned within the interior volume of the hollow outer cylinder thereby defining an annular volume between the exterior surface of the inner cylinder and the interior surface of the hollow outer cylinder.

Optionally, substantially the majority of the elastic support member is retained within the annular volume when the elastic support member is in the retracted state.

Optionally, the inner cylinder is a hollow cylinder further including an interior surface defining an interior volume for retaining at least a portion of a component of the device selected from the group consisting of: a motor for driving the electro-mechanical drive arrangement, the control unit, and one or more sensors associated with the control unit.

Optionally, the device further comprises one or more sensors associated with the control unit, the one or more sensors selected from the group consisting of a pressure senor, a temperature sensor, a humidity sensor, a blood pressure sensor, an audio sensor, a vibration sensor, a tissue contact sensor, an optical peripheral capillary oxygen saturation sensor, an electromyography sensor, a force sensor, and an elastic support member integrity sensor.

Optionally, each of the one or more sensors is configured to provide signals to the control unit, and the control unit is configured to actuate or refrain from actuating the electro-mechanical drive arrangement to move the elastic support member according to at least one rule.

Optionally, the at least one rule is selected from the group consisting of: moving the elastic support member to the deployed state if the user is experiencing a respiratory event, moving the elastic support member to the deployed state if the user is asleep, moving the elastic support member to the deployed state after a predetermined elapsed period of time, moving the elastic support member to the retracted state after a predetermined elapsed period of time, refraining from moving the elastic support member to the deployed state is the user is awake, refraining from moving the elastic support member to the deployed state if the user is not experiencing a respiratory event, refraining from moving the elastic support member if the integrity of the elastic support member is compromised.

Optionally, the device further comprises a power supply deployed to provide power to at least one of the electro-mechanical drive arrangement and the control unit.

Optionally, the power supply is a rechargeable power supply.

Optionally, the device further comprises a charging arrangement configured to come into operative cooperation with the rechargeable power supply.

Optionally, the base member includes a substantially arcuate perimeter surface that includes first and second branches.

Optionally, the base member further includes a band having first and second ends, the first end fixedly coupled to the first branch and the second end fixedly coupled to the second branch, such that the band extends laterally across the base member, and the elastic support member is fixedly coupled to at least a portion of the band.

Optionally, the elastic support member, the electro-mechanical drive arrangement, and the control unit are retained within a single housing.

Optionally, the single housing is retained within the mouth of the user when the base member is coupled to the upper or lower jaw of the user.

Optionally, the region of tissue includes at least a portion of the pharynx.

Optionally, when the elastic support member is in the deployed state, the elastic support member provides a force profile to the region of tissue that includes a radial component of force.

Optionally, the base member includes a plurality of anchoring members, each respective anchoring member for removably attaching to a respective tooth or tooth pair of the user.

Optionally, each of the anchoring members includes a mold of the respective tooth or tooth pair.

There is also provided according to an embodiment of the teachings of the present invention, a device for reducing breathing Obstructions of a user, the device comprising: a base member for removably coupling to the upper or lower jaw of the user; an elastic support member operatively coupled to the base member, the elastic support member including at least one contact surface for contacting a region of tissue, the elastic support member operative to assume a range of volumes between an initial volume, in which the at least one contact surface is spatially separated from the region of tissue, and a second volume, in which at least a portion of the elastic support member is extended, such that the at least one contact surface contacts the region of tissue and the elastic support member provides a force profile to the region of tissue to prevent at least partial collapse of at least a section of the upper airway, the initial volume being at least half of the second volume; an electro-mechanical drive arrangement in mechanical driving relationship with the elastic support member; and a control unit associated with the electro-mechanical drive arrangement, the control unit configured for actuating the electro-mechanical drive arrangement to adjust the volume of the elastic support member.

There is also provided according to an embodiment of the teachings of the present invention, a device for reducing breathing obstructions of a user, the device comprising: a base member for removably coupling to the upper or lower jaw of the user; an elastic support member operatively coupled to the base member, the elastic support member including at least one contact surface for contacting a region of tissue, the elastic support member operative to assume a range of lengths between an initial length, in which the at least one contact surface is spatially separated from the region of tissue, and a second length, in which at least a portion of the elastic support member is extended, such that the at least one contact surface contacts the region of tissue and the elastic support member provides a force profile to the region of tissue to prevent at least partial collapse of at least a section of the upper airway; an electro-mechanical drive arrangement in mechanical driving relationship with the elastic support member; and a control unit associated with the electro mechanical drive arrangement, the control unit configured for actuating the electro-mechanical drive arrangement to adjust the length of the elastic support member.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIG. 6 is a block diagram of some of the elements of the electro-mechanical assembly and a bedside unit for removably coupling to the intra-oral device, constructed and operative according to an embodiment of the invention.

DESCRIPTION OF THE PREFERRED EMBODIMENTS

Figure 1A:
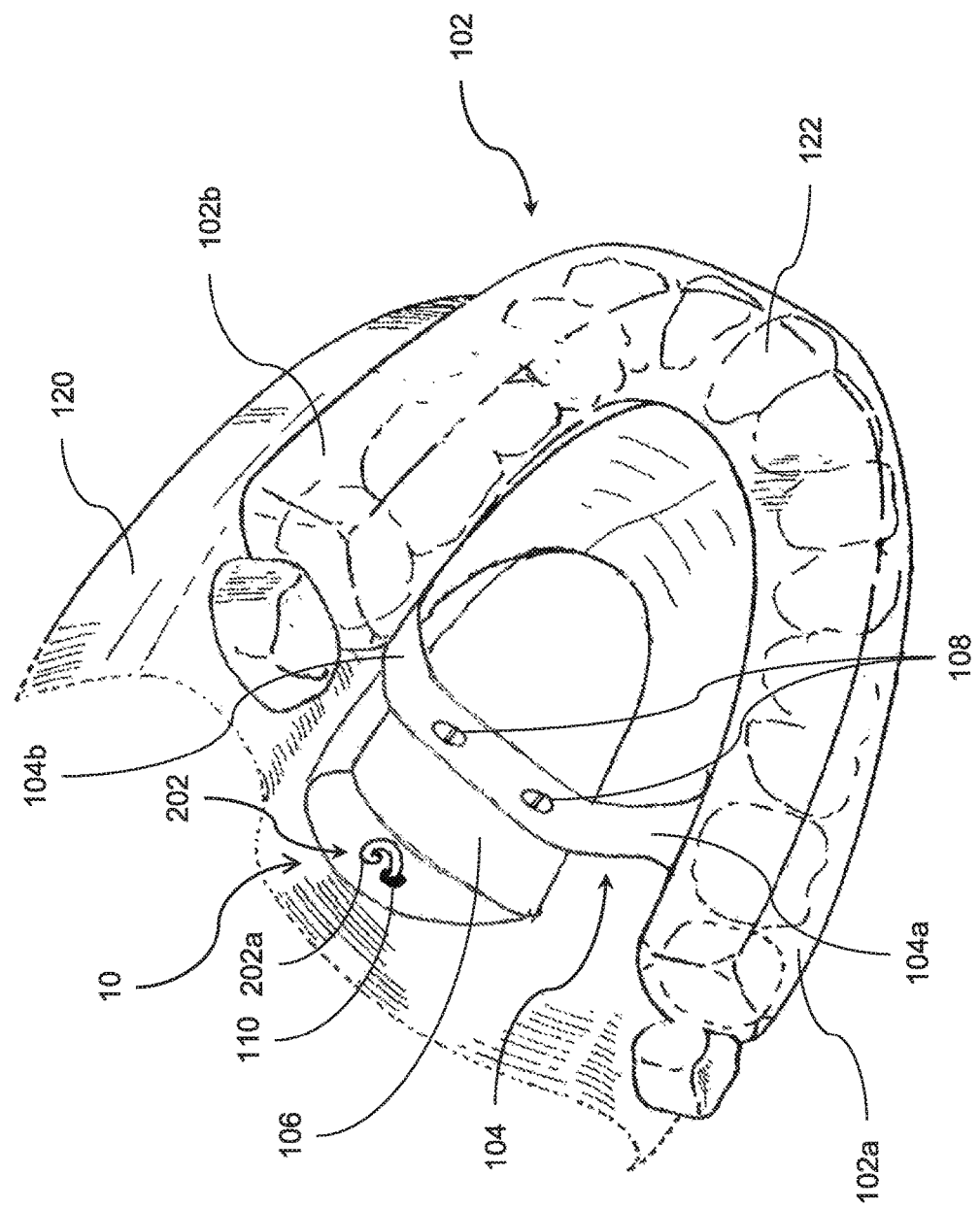
FIG. 1A is an isometric view illustrating a schematic representation of an intra-oral device secured to the upper jaw of a user, constructed and operative according to an embodiment of the invention, with an elastic support member in a retracted state.

The present invention is an intra-oral device for providing upper airway support to reduce breathing obstructions.

The principles and operation of the intra-oral device according to the present invention may be better understood with reference to the drawings and accompanying description.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways. Initially, throughout this document, references are made to directions such as, for example, upper and lower, proximal and distal, upward and downward, clockwise and counter clockwise, right, left, and the like. These directional references are exemplary only to illustrate the invention and embodiments thereof. The terms "proximal" and "distal" are used in their normal senses to relate to the portions of the intra-oral device closer and further, respectively, to the lips of the user during use of the intra-oral device.

Figure 1C:
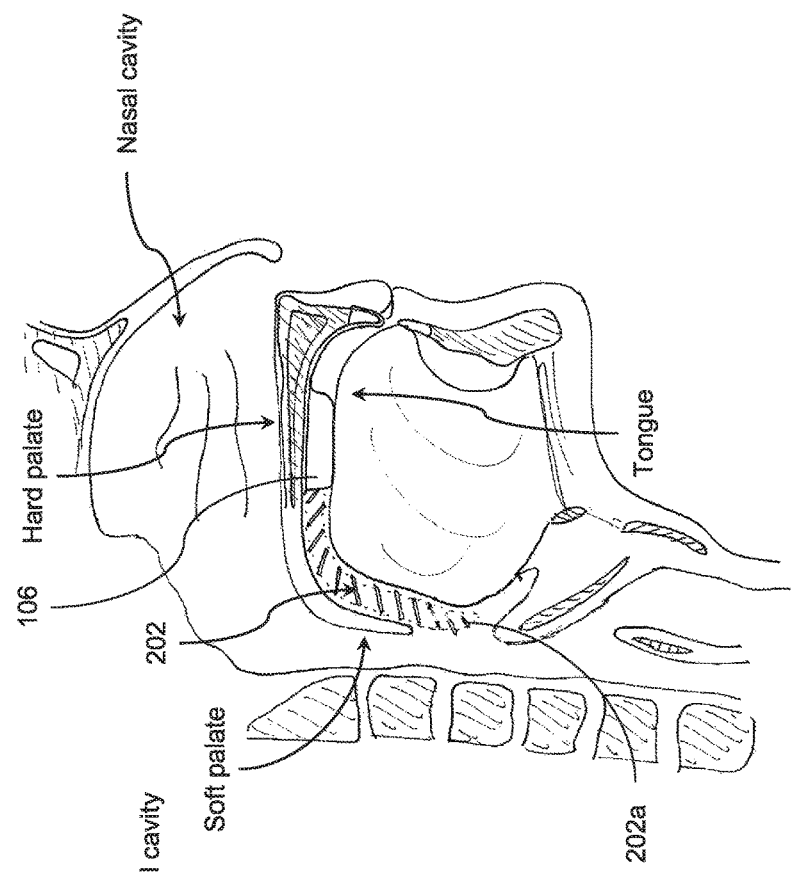
FIGS. 1B and 1C are side views illustrating schematic representations of the intra-oral device secured to the upper jaw of a user, constructed and operative according to an embodiment of the invention, with the elastic support member in a deployed state at an initial deployed length and a maximum deployed length, respectively.
Figure 1B:
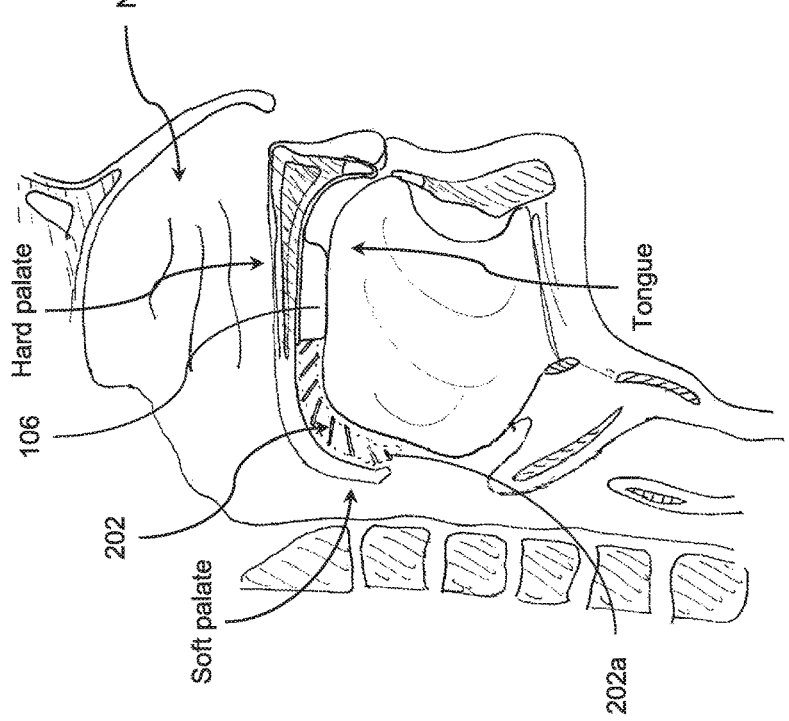

Referring now to FIGS. 1A-1C of the drawings, an embodiment of an intra-oral device 10 secured within the mouth of a user. The mouth of the user includes the upper jaw 120 which carries a set of teeth 122, which may be, .for example, the natural teeth of the user, teeth surgically implanted in the jaw 120, or removable dentures. The intra-oral device 10 includes a base member 102 for securing to teeth 122 of the user, a band 104 connected to the base member 102, and a moisture sealed enclosure 106 connected to the hand 104 for housing an electro-mechanical assembly 200 which provides upper airway support to the user. Within the context of this document, the term "upper airway" generally refers to the section of the respiratory tract that includes sections of the pharynx, such as the oropharynx and nasopharynx, and may also include the nose and nasal passages, paranasal sinuses, and portions of the larynx above the vocal cords. Although the intra-oral device 10 is depicted as securing to the teeth in the upper jaw of the user, it should be understood to one of ordinary skill in the art that the intra-oral device 10 may be similarly desired and manufactured to secure to the teeth in the lower jaw of the user.

In a non-limiting implementation, the base member 102 is formed from an acrylic based arcuate mold of the teeth 122 of the user. The base member 102 may be designed according to well accepted design standards in the medical and dental industries for intra-oral devices, such as, for example, teeth realignment devices, devices for bruxism treatment, or devices for mandibular advancement. The base member 102 is preferably manufactured from a hard plastic, but may also be manufactured from any other suitable material for intra-oral use, including, but not limited to, metal based materials and the like. In such a non-limiting implementation, the base member 102 is manufactured to match elements of the mouth of the user in both size and shape, and includes anchoring mechanisms, such as, for example, ball clasps or vacuum based tight fitting acrylic dental impression molds, for securing to the teeth 122. As such, the base member 102 can be easily secured to, and removed from, the mouth of the user. The base member 102 may additionally be formed such that the mouth of the user is maintained slightly agape when the base member 102 is secured to the teeth 122, providing increased space in the oral cavity for positioning the enclosure 106 and the electro-mechanical assembly 200. Within the context of this document, the term "oral cavity" generally refers to the sections of the mouth that include the inside lining of the lips, the buccal mucosa, the teeth and gums, the majority of the tongue, the floor of the mouth below the tongue, the hard palate, sections of the soft palate, and the oropharynx, which generally includes the tissue of the soft palate as well as the distal portions of the tongue.

The band 104 includes two ends, a first end 104a and a second end 104b, and extends laterally, from left to right, across the base member 102. In the non-limiting arcuate mold implementation of the base member 102, the base member 102 includes two branches, a first branch 102a and a second branch 102b. Each branch extends along the arcuate perimeter of the based member 102 towards the location of respective molars in the upper jaw 120, and includes anchoring mechanisms for securing to the teeth 122 in the upper jaw 120. Each of the anchoring mechanisms is configured to secure to a respective tooth, or pair of teeth, in the upper jaw 120. The band 104 is secured to the base member 102 by connecting the first end 104a to the first branch 104a and connecting the second end 104b to the second branch 102b. The base member 102 and the band 104 may be formed from a single body, or may formed from separate bodies and connected by any suitable technique, including, but not limited to, adhesive or epoxy bonding techniques.

The band 104 is preferably arcuate in shape, and forms an arc that protrudes upwards towards the hard palate of the user. A gap of approximately 8 millimeters is maintained between the hard palate and sections of the band 104 closest in distance to the hard palate to allow for the installation of the enclosure 106. in embodiments in which the base member 102 is secured to the teeth in the lower jaw, the arc of the band 104 protrudes upwards at a higher degree to minimize contact between the band 104 and the tongue. The enclosure 106 is connected to the band 104 via metallic screws 108, the heads of which are shown in FIG. 1A. The metallic screws 108 may also serve as electrical contact points for charging the electrical components of the electro-mechanical assembly 200 housed within the enclosure 106, without breaching the moisture seal of the enclosure 106. Although two metallic screws 108 are depicted in FIG. 1A, more than two such metallic screws may be used to secure the enclosure 106 to the band 104. Note that alternative fastening techniques for connecting the enclosure 106 the band 104 may be used, including, but not limited to, adhesive or epoxy bonding techniques.

Note that alternatively, the space between the branches 102a and 102b may be filled with a layer or layers of material, such as, for example, hard plastic or the like. As such, the enclosure 106 may be directly attached to the material layer between the branches 102a and 102b without necessitating the use of the band 104 for attaching the enclosure 106 to the base member 102.

The enclosure 106 is preferably manufactured with an outer surface coated with or firmed by a bio-compatible material appropriate for extended intra-oral use, such as for example, acrylic resins commonly used in the medical and dental industries. Furthermore, the edges of the enclosure 106 are preferably rounded and smooth to reduce discomfort, and prevent injury to tissue and muscles in the oral cavity, such as the tongue, gums, hard palate and sections of the soft palate. The enclosure 106 may be manufactured to match the palate of the user in both size and shape, such that the upper surface of the enclosure 106 matches the general curvature of the hard palate. Additionally, the enclosure 106 is preferably of sufficiently small volume, such that the intra-oral device 10 does not provide discomfort to the user. Accordingly, the enclosure is preferably approximately 25 millimeters in length, 15 millimeters in width, and 8 millimeters in height, Such dimensions allow the intra-oral device 10, and more particularly the enclosure 106, to rest comfortably between the hard palate and the tongue of the user, when inserted in the mouth.

As mentioned above, the enclosure 106 houses an electro-mechanical assembly 200 which provides upper airway support to the user, and reduces breathing obstructions, such as those induced by the onset of OSA.

Attention is now directed to FIGS. 3A-6, which shows details of the elements of the electro-mechanical assembly 200. In describing the elements of the electro-mechanical assembly 200, reference is also made to the elements shown in FIGS. 1A-1C. The electro-mechanical assembly 200 includes an elastic support member 202 which acts as a retractable and deployable stent for placement in the upper airway, an electro-mechanical drive arrangement 210 for retracting and deploying the elastic support member 202, a control unit 204 for actuating the electro-mechanical drive arrangement 210, and a power supply 206. The elastic support member 202 may be designed to be replaceable, providing the user with the option of replacing the elastic support member 202 after extended use. This serves as a form of preventative maintenance, reducing the risk of malfunction of the elastic support member 202 after extended periods of use. The elastic support member 202 is moveable between two states, a retracted state (FIGS. 1A and 3A) and a deployed state (FIGS. 1B, 1C and 3B). As will further be described in more detail below, the electro-mechanical drive arrangement 210 provides power and mechanical drive, based on control input from the control unit 204, to move the elastic support member 202 between the two states.

As shown in FIG. 6, the control unit 204 includes at least one processor 205 coupled to a storage medium 208 such as a memory or the like. The processor 205 is also preferably coupled to an analog to digital conversion (ADC) module 207 for receiving analog input and providing digitized output to the processor 205. The processor 205 can be any number of computer processors, including, but not limited to, a microcontroller, a microprocessor, an ASIC, a DSP, and a state machine. Such processors include, or may be in communication with computer readable media, which stores program code or instruction sets that, when executed by the processor, cause the processor to perform actions. Types of computer readable media include, but are not limited to, electronic, optical, magnetic, or other storage or transmission devices capable of providing a processor with computer readable instructions.

Figure 3A:
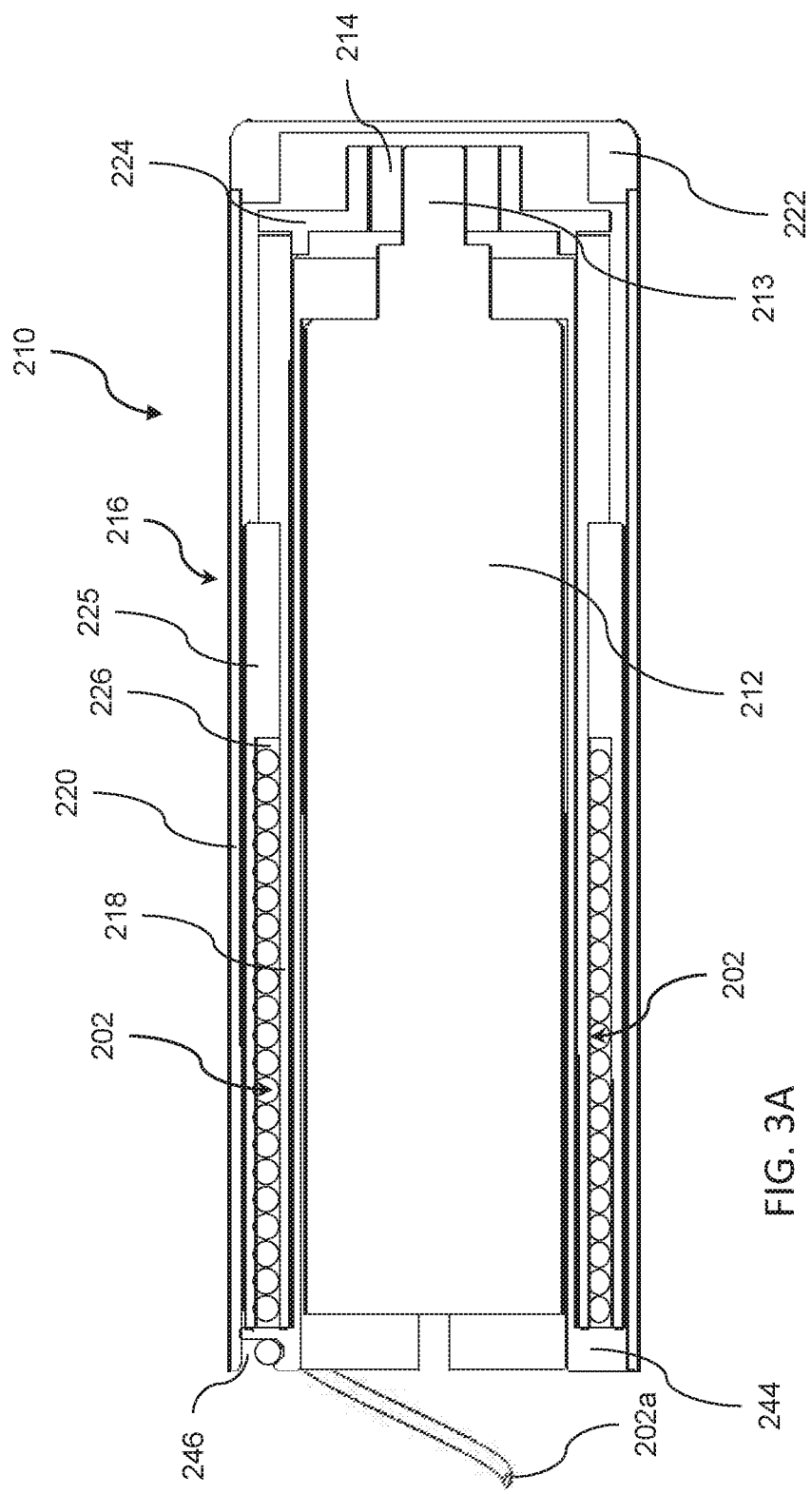
FIGS. 3A and 3B are cross-sectional views of an electro-mechanical assembly of the intra-oral device, constructed and operative according to an embodiment of the invention, with the elastic support member in the retracted state and the deployed state at the maximum deployed length, respectively.

As shown in FIGS. 1A and 3A, when the elastic support member 202 is in the retracted state, almost the entirety of the elastic support member 202 is enclosed and retained within the enclosure 106, except for the distal end 202a of the elastic support member 202 and portions of the elastic support member 202 proximate to the distal end 202a, which protrude slightly through a hole 110 in the distal end of the enclosure 106. The length, along the longitudinal axis of the elastic support member 202, of the portions of the elastic support member 202 which protrude through the hole 110 when in the retracted state, is approximately in the range of 5-10 millimeters Furthermore, a special separation in the range of approximately 5-15 millimeters is provided between the region of contact tissue the portion of the walls of the upper airway) and the distal end 202a when the base member 102 is secured to the mouth of the user and the elastic support member 202 is in the retracted state. Accordingly, when the intra-oral device 10 is initially positioned in the mouth of the user with the elastic support member 202 retracted, no portions of the elastic support member 202 make any contact with regions of tissue in the oral cavity and/or the upper airway which may stimulate the gag reflex.

Although not shown in FIG. 1A, when in the retracted state, almost the entirety of the elastic support member 202 is preferably enclosed and retained within a casing, which is permanently and entirely retained within the enclosure 106. Such a casing will be described in further detail below with reference to non-limiting exemplary implementations of the elastic support member 202 and the electro-mechanical drive arrangement 210.

When the elastic support member 202 moves from the retracted state to the deployed state, the elastic support member 202 increases in length, and in certain embodiments increases in diameter and volume as well, resulting from the movement out of the enclosure 106 through the hole 110. The hole 110 is typically sealed with an elastic annular seal that allows the elastic support member 202 to move in and out of the enclosure 106 while preventing excess amounts of moisture from permeating the enclosure 106 and coming into contact with electronic and mechanical components, such as the power supply 206, the control unit 204, and components of the electro-mechanical drive arrangement 210. Alternatively, the elastic support member 202 is retracted and deployed from a separate compartment within the enclosure 106, which is fluidically-isolated from the compartment holding the electronic and mechanical components.

As shown in FIGS. 1B and 1C, when the elastic support member 202 is in the deployed state, the distal end 202a and/or other portions of the elastic support member 202 contact regions of tissue in the oral cavity and/or the upper airway of the user, such as the oropharynx and nasopharynx, and more specifically sections of tissue of the soft palate. The elastic support member 202 applies radial forces to the region of contact tissue (i.e., the walls of the upper airway) which prevents the collapse of the airway from the weight of the surrounding tissue and from the reduced atmospheric pressure in the airway. As a result, the elastic support member 202, when in the deployed state, maintains the integrity of the upper airway of the user and prevents the full or partial collapse of the upper airway induced by the onset of OSA or similar disorders.

Note that as the elastic support member 202 lengthens, due to movement from the retracted state to the deployed state, the elastic support member 202 bends with the curvature of the soft palate, as illustrated in FIGS. 1B and 1C. It is also noted that the elastic support member 202 is defined to be in the deployed state when the distal end 202a and/or other portions of the elastic support member 202 make contact with the above mentioned regions of tissue, such that elastic support member 202 applies appropriate radial forces to the regions of tissue, in the oral cavity and/or the upper airway of the user. Accordingly, the length of the elastic support member 202 may continue to increase, as driven by the electro-mechanical drive arrangement 210 under actuation by the control unit 204, while in the deployed state until reaching a maximum deployed length. As such, the elastic support member 202 may assume a range of lengths, between an initial deployed length and a maximum deployed length, while in the deployed state. Examples of the elastic support member 202 assuming an initial deployed length and a maximum deployed length are illustrated in FIGS. 1B and 1C, respectively.

It is noted that the example lengths of the initial deployed length and maximum deployed length as depicted in FIGS. 1B and 1C, respectively, are strictly illustrations intended to provide a better understanding of the functionality of the components of the intra-oral device 10 described herein. As should be understood, in practice the initial deployed length may be shorter or longer than the initial deployed length illustrated in FIG. 1B, and the maximum deployed length may be shorter or longer than the maximum deployed length illustrated in FIG. 1C.

It is also noted that the elastic support member 202 is defined to be in the retracted state when the distal end 202a and/or any other portions of the elastic support member 202 refrain from making contact with the region of contact tissue in the oral cavity and/or the upper airway of the user, or any other regions of tissue and/or muscles in the mouth, and/or the oral cavity, and/or the upper airway. As mentioned above, the distal end 202a is spatially separated from the region of contact tissue by approximately 5-15 millimeters when in the retracted state. Accordingly, the length of the elastic support member 202 may continue to decrease from a length that promotes 5 millimeters of spatial separation between the distal end 202a and the region of contact tissue, to a length that promotes 15 millimeters of spatial separation, while being defined to be in the retracted state.

Figure 2:
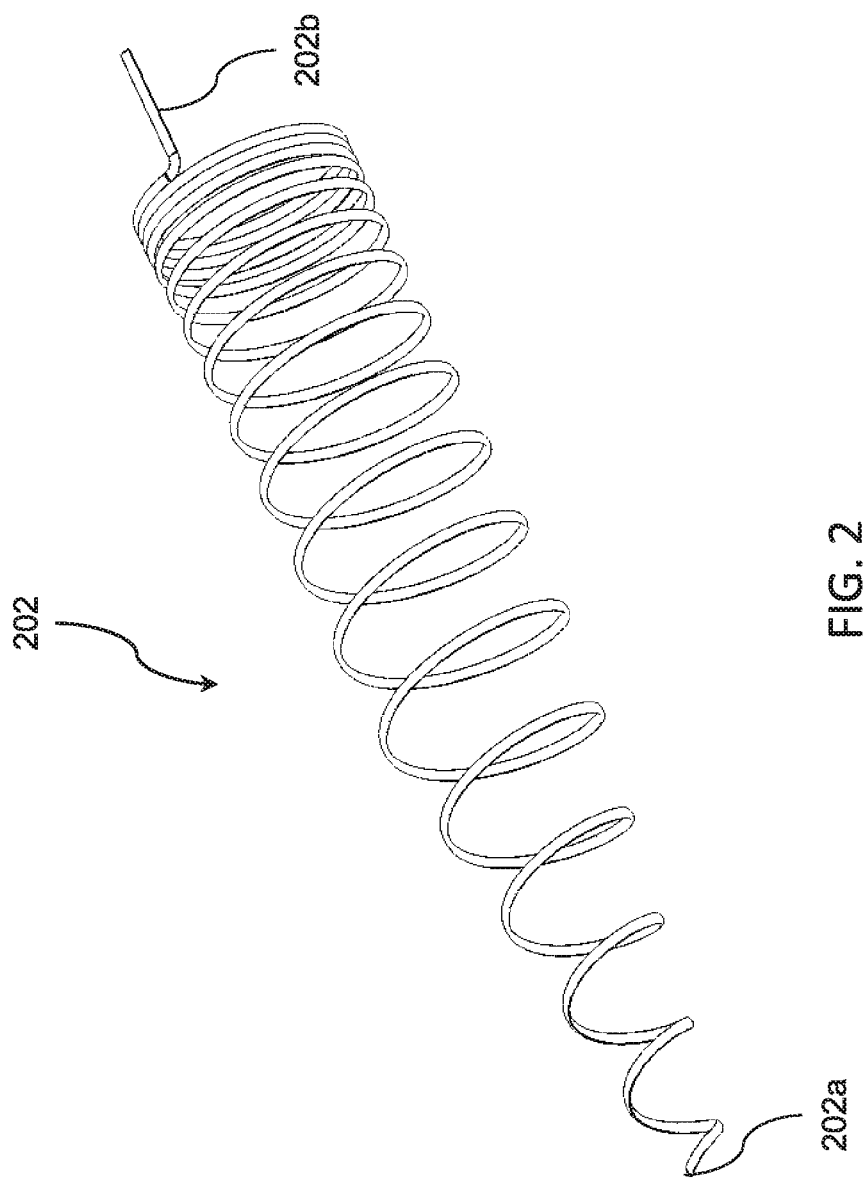
FIG. 2 is a perspective view of an implementation of the elastic support member as a helical spring, constructed and operative according to an embodiment of the invention.

Refer now to FIG. 2, a non-limiting exemplary implementation of the elastic support member 202. In such an implementation, the elastic support member 202 is formed as a helical spring which has a generally rounded edged rectangular cross-sectional shape along the majority of the length of the helical spring 202. Movement of the helical spring 202 between the retracted and deployed states is induced by rotation of the helical spring 202 about its longitudinal axis.

For clarity of illustration, the remainder of the present disclosure describes the components of the intra-oral device 10 with reference to the elastic support member 202 implemented as a helical spring. It is noted herein, that the elastic support member 202 may be formed as any suitable shape which can provide support and prevent collapse as mentioned above while still allowing the retraction into the enclosure 106, such as, for example, a cylinder-like structure or a plate-like structure, and that the helical spring structure of the elastic support member 202 should not limit the functionality of other components of the intra-oral device 10 to the functionality described with respect to the exemplary helical spring structure implementation.

The helical spring 292 is formed by a wire, such as, for example, Nitinol wire, which is wound to generate the coils of the helical spring 202. Within the context of this document, the term "coil" is used interchangeably with the term "loop", and refers to individual ring shaped sections of the spring. The helical spring includes a proximal end 202b and the distal end 202a which is preferably formed into a rounded soft end to prevent injury to soft tissue in the oral cavity and/or upper airway when the elastic support member 202 moves between the retracted and deployed states. Each of the coils along a majority of the length of the helical spring has approximately equal diameter. According to a non-limiting implementation as illustrated in FIG. 2, the diameter of the last few coils gradually decrease near the distal end 202a, resulting in a generally rounded conical cross-section. As a result, the coil closest in proximity to the distal end 202a has the smallest diameter of all of the coils of the helical spring 202. Such an implementation allows for helical spring 202 to thread through small openings in the oral cavity and upper airway, such as between the tongue and the soft palate.

The helical spring 202 preferably includes approximately 10-15 coils. When in the deployed state (i.e., when the spring is at least partially relaxed), the spacing between adjacent coils is approximately 4-15 millimeters, and more preferably approximately 7-10 millimeters. Note that the spacing between pairs of adjacent coils is not necessarily uniform. The helical spring 202 has a variable length in the range of approximately 40-150 millimeters, and more preferably in the range of 40-120 millimeters. The minimum length of the helical spring 202 is the length of the spring when in the retracted sate (i.e., when the spring is fully compressed).

Similarly, the maximum deployed length of the helical spring 202 is the maximum length of the spring when in the deployed state. As such, the helical spring 202 can achieve a length in the retracted state that is approximately 5-15% of the maximum deployed length. Furthermore, each coil of the helical spring 202 preferably has a variable diameter in the range of approximately 5-15 millimeters, and more preferably in the range of 5-10 millimeters. The minimum diameter of the helical spring 202 is the diameter of the spring when in the retracted state. Similarly, the maximum deployed diameter of the helical spring 202 is the maximum diameter of the spring when in the deployed state. As such, the helical spring 202 can achieve a diameter in the retracted state that is approximately 30% of the maximum deployed diameter. As a result of the compressibility of the helical spring 202 in both length and diameter, the helical spring 202 is compressible to a small volume as needed, preferably to a volume less than 10% of the original volume, and most preferably to a volume less than 5% of the original volume.

When in the deployed state, the helical spring 202 allows an air passage along the longitudinal axis with a free cross-sectional area at any point along the length of the spring. Preferably, the cross-sectional area is in the range of 20-200 square millimeters, and more preferably in the range of 40-200 square millimeters. As mentioned above, the helical spring 202 is compressible in both length and diameter. As such, the helical spring 202 has a variable cross-sectional area along the length of the spring. Preferably, the helical spring 202 maintains at least 50% of the maximum cross-sectional area along the entire length of the helical spring 202 under an evenly distributed tangential pressure of at least 0.3 pounds per square inch (psi), but not more than 0.5 psi. It is noted that drops in atmospheric pressure in the oral cavity are typically due to fluid flow, such as, for example, inhalation of air and swallowing of saliva. As such, the above preferred ranges of cross-sectional area are intended to withstand tangential pressures due to fluid flow at a rate of approximately 4 liters per sec.

The portion of the helical spring 202 that is deployed from the enclosure 106 increases in length, when moving from the retracted state to the deployed state, at a rate in the range of approximately 0.5-20 millimeters per minute. The relatively slow deployment allows the nerves in the oral cavity, more specifically, at the base of the tongue, that stimulate the gag reflex sufficient time to habituate to the contact between the helical spring 202 and the tissue in the oral cavity and/or upper airway. Accordingly, a helical spring 202 having a maximum deployed length of 100 millimeters may reach the full length after an elapsed time of 5-200 minutes, with an average elapsed time to maximum deployed length of approximately 30 minutes.

The helical spring 202 is preferably coated with a low friction material suitable for intra-oral use, such as, for example, silicone, Polytetrafluoroethylene (PTFE) or the like. The low friction material coating preferably has a coating thickness in the range of approximately 50-300 microns. The low friction material coating reduces the coefficient of friction between the helical spring 202 and the region of contact tissue in the mouth of the user, lessening the risk of erosion or pressure wounds. Furthermore, in the event of malfunction or damage to the helical spring 202 during use, the coating maintains the integrity of the helical spring 202 and allows the electro-mechanical drive arrangement 210 to retract the helical spring 202, or the user to remove the intra-oral device 10 from the mouth without debris from components of the intra-oral device 10 being maintained in the mouth of the user. Additionally, the low friction material coating decreases the rate of buildup of residue and other materials on the helical spring 202 over time.

As previously mentioned, the electro-mechanical drive arrangement 210 provides power and mechanical drive to move the helical spring 202 between the retracted and deployed states. The electro-mechanical drive arrangement 210 preferably includes a retraction and deployment mechanism 216, an electric motor 212 for driving the retraction and deployment mechanism 216, and a gear 214.

The electric motor is of sufficiently small enough size to fit inside the size of the enclosure 106 as described above. For the purposes of this document, power supplies and devices operating on voltages of no more than 12 volts direct current (DC) are termed "low voltage", while power supplies of at least 100 volts alternating current (AC) are defined as "mains voltage power supplies". In more specific terms, a mains voltage power supply in the United States typically supplies power in the range of 100-120 volts AC, while a mains voltage power supply in Europe typically supplies power in the range of 220-240 volts AC. Accordingly, it is preferred that the electric motor 212 is a direct current (DC) electric motor that receives DC voltage, preferably from the power supply 206, as input. Examples of such DC electric motors include, but are not limited to, 3-volt DC electric motors such as those produced by Marswell Engineering Ltd. of Hong Kong.

The power supply 206 is preferably implemented as a low voltage rechargeable battery with a maximum voltage of 12 volts DC. In such an implementation, the metallic screws 108 provide electrical contact points with the rechargeable power supply 206. As such, a charging arrangement 302, coupled to a bedside unit 300, connected to a mains voltage power supply, may be configured to recharge the rechargeable power supply 206 via the metallic screws 108. Alternatively, a charging interface, such as, for example, charging cables or other suitable electrical connections, may be used to recharge the rechargeable power supply 206. Alternatively, the power supply 206 may be a non-rechargeable power supply (i.e., a replaceable power supply), such as a disposable battery.

The electric motor 212 drives the retraction and deployment mechanism 216 through the gear 214 that is positioned on a shaft 213 of the electric motor 212. Typically, electric motors provide nominally high revolutions per minute (RPM) and low torque output. Accordingly, the gear 214 converts the high RPM and low torque output from the electric motor 212 to low RPM and high torque necessary to drive the retraction and deployment mechanism 216 at the desired retraction and deployment rate. A torque sensor (not shown) may be placed at the output of the gear 214 to verify proper functionality of the electro-mechanical drive arrangement 210.

Refer now to FIGS. 3A-5, a non-limiting exemplary implementation of the retraction and deployment mechanism 216. In such an implementation, the retraction and deployment mechanism 216 is implemented as a cylinder arrangement that drives the deployment of the helical spring 202 and houses the helical spring 202 when in the retracted state. FIGS. 3A and 3B show cross-sectional views of the retraction and deployment mechanism 216 with the helical spring 202 in the retracted and deployed states, respectively. For clarity of illustration, the helical spring 202 is not shown in FIGS. 4 and 5.

The cylinder arrangement includes a hollow inner cylinder 218, a hollow outer cylinder 220, and a release plate 240 for guiding the retraction and deployment of the helical spring 202 from the retraction and deployment mechanism 216 through the hole 110. Preferably, the hollow inner cylinder 218 has a diameter of approximately 4.5 millimeters, and the hollow outer cylinder has a diameter of approximately 5.5 millimeters.

The release plate 240 includes a generally hollow cylindrical section 242 having an interior surface defining an interior volume, and a flange 244 at the distal end of the release plate 240. The release plate 240 also includes a generally curved slot 246 extending partially through the flange 244, for allowing passage of the helical spring 202 in and out of the cylinder arrangement during movement between the retracted and deployed states.

Each of the cylinders 218 and 220 has a respective interior and exterior surface, with each of the interior surfaces defining a respective interior volume. The hollow cylindrical section 242 of the release plate 240 is positioned within the interior volume of the hollow inner cylinder 218. In a non-limiting implementation, the electric motor 212 is positioned within the interior volume defined by the interior surface of the hollow cylindrical section 242 of the release plate 240. In such an implementation, the shaft 213 passes through an opening in the proximal end of the release plate 240. Accordingly, in such an implementation, the electric motor 212 and corresponding components thereof are considered part of the retraction and deployment mechanism 216.

The hollow inner cylinder 218 is positioned within the interior volume defined by the interior surface of the hollow outer cylinder 220. As a result, when the hollow inner cylinder 218 is positioned within the interior volume of the hollow outer cylinder 220 an annular space 226 is provided between the exterior surface of the hollow inner cylinder 218 and the interior surface of the hollow outer cylinder 220. The annular space 226 extends along a portion of the length of the hollow inner cylinder 218 between the distal end of the cylinder arrangement and a flange 219 of the hollow inner cylinder 218. It is preferred that the length of the helical spring 202, when maximally compressed, is longer than the length for which the annular space 226 extends allowing protrusion of the distal end 202a as described above.

When in the retracted state, the helical spring 202 is wound around the exterior surface of the inner hollow cylinder 218 and compressed and entirely housed, except for the distal end 202a and portions of the elastic support member 202 proximate to the distal end 202a, in the annular space 226 between the exterior surface of the hollow inner cylinder 218 and the interior surface of the hollow outer cylinder 220. As the hollow cylindrical section 242 of the release plate 240 is positioned within the interior volume of the hollow inner cylinder 218, the flange 244 provides a cover to the opening of the annular space 226 in the distal end of the cylinder arrangement, preventing the helical spring 202 from escaping entirely out of the annular space 226. A portion of the curved slot 246 is coupled to the annular space 226, providing a pathway for the helical spring 202 to move into and out of the cylinder arrangement, during movement between the retracted and deployed states.

Figure 3B:
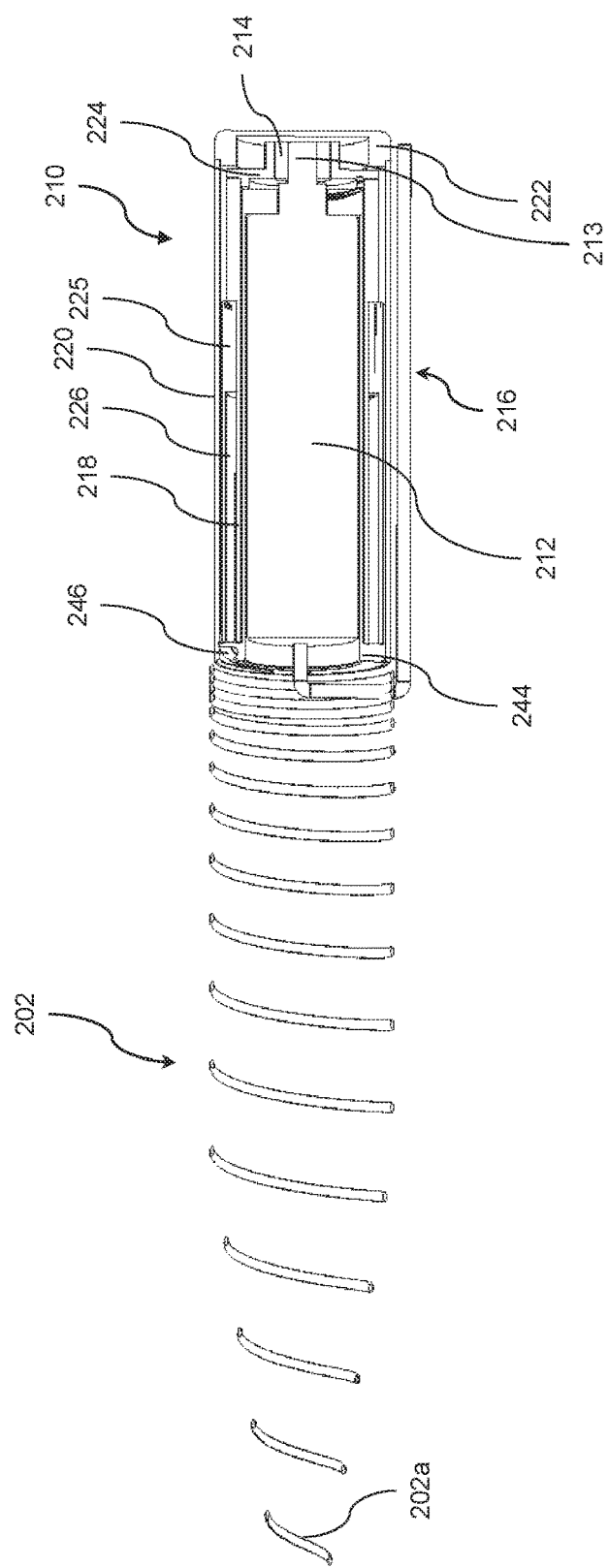
Figure 4:
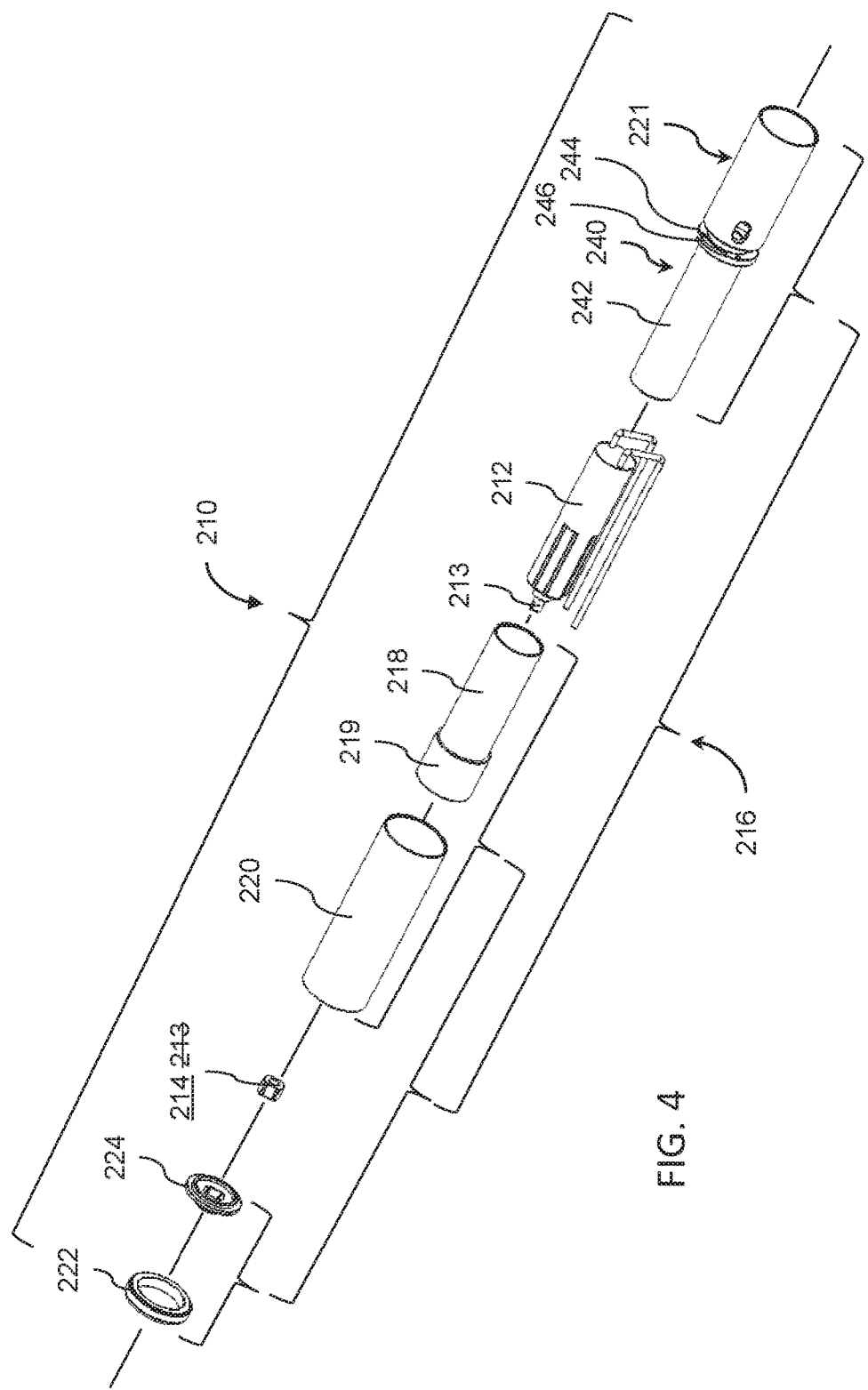
FIG. 4 is an isometric exploded view of some of the elements of the electro-mechanical assembly, constructed and operative according to an embodiment of the invention.
Figure 5:
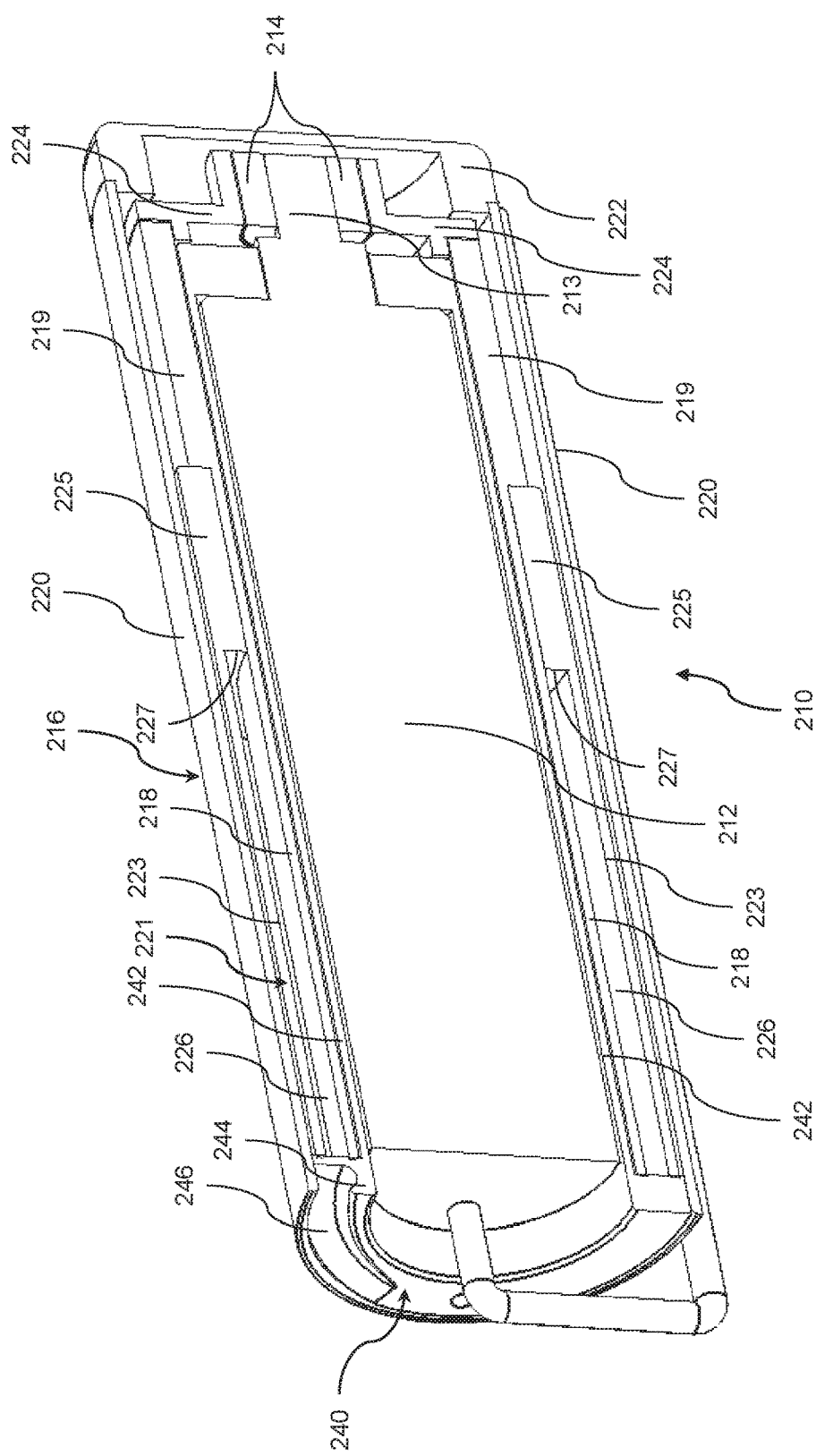
FIG. 5 is an isometric cross-sectional view of some of the elements of the electro-mechanical assembly, constructed and operative according to an embodiment of the invention.

The flange 219 extends over approximately the last ¼ of the length of the hollow inner cylinder 218 towards the proximal end of the cylinder arrangement. The proximal end 202b of the helical spring 202 is dimensioned and oriented to prevent the distal end 202 from passing through the curved slot 246, preventing the helical spring 202 from fully separating from the cylinder arrangement. As such, the proximal end 202b of the helical spring 202 is permanently retained within the annular space 226 during movement between the retracted and deployed states. For example, as depicted in FIGS. 2 and 3B, the proximal end 202b is dimensioned and oriented to be parallel to the longitudinal axis of the helical spring 202. Accordingly, the retraction and deployment mechanism 216, when implemented as such a cylinder arrangement, further acts as the casing, for enclosing and retaining almost the entirety of the helical spring 202, which is permanently and entirely retained within the enclosure 106, as briefly discussed above.

In a non-limiting implementation, the cylinder arrangement may further include a hollow intermediate cylinder 221 having an interior and an exterior surface, with the interior surface defining an interior volume. In such an implementation, the hollow inner cylinder 218 is positioned within the interior volume defined by the interior surface of the hollow intermediate cylinder 221, and the hollow intermediate cylinder 221 is positioned within the interior volume defined by the interior surface of the hollow outer cylinder 220.

The hollow intermediate cylinder 221 includes two sections having two differing internal diameters, namely a main section 223 having a first internal diameter, and an indented section 225 having a second internal diameter. The first internal diameter is larger than the second internal diameter. The location within the hollow intermediate cylinder 221 in which the change in internal diameter occurs forms a step 227 defining the farthest point the proximal end 202b of the helical spring 202 can be positioned in the annular space 226. The use of the hollow intermediate cylinder 221 results in a more compressed helical spring 202 in the retracted state, A cylinder cover 222 connects to, and covers, both of the cylinders 218 and 220 at the proximal ends of the cylinders 218 and 220, fixedly maintaining the electric motor 212 within the release plate 240, the hollow cylindrical section 242 of the release plate 240 within the hollow inner cylinder 218, and the hollow inner cylinder 218 within the hollow outer cylinder 220. The cylinder cover 222 also connects to, and covers, the gear 214 via a gear cover 224. Additional fasteners may be used to fortify the fixedly nested placement of the electric motor 212, the hollow inner cylinder 218, and the hollow outer cylinder 220.

As a result of the above described interconnection of the components of the cylinder arrangement, actuation of the electric motor 212, by the control unit 204, causes the rotation of the shaft 213 which in turn causes rotation of both of the cylinders 218 and 220. Accordingly, the cylinders 218 and 220 rotate as a single body, which causes the helical spring 202 to rotate about the longitudinal axis of the helical spring 202.

As mentioned above, the annular space 226 and the curved slot 246 provide a path for the passage of the helical spring 202 in and out of the cylinder arrangement during movement between the retracted and deployed states. Accordingly, rotation of the cylinders 218 and 220 causes the helical spring 202 to lengthen or shorten and the distal end 202a to extend out of, or retreat into, the cylinder arrangement through the curved slot 246 via the hole 110, when moving between the retraced state and the deployed state.

Movement from the retracted state to the deployed state is caused by actuation of the electric motor 212, by the control unit 204, which causes the cylinder arrangement to rotate in a clockwise direction of rotation (when viewed from the proximal end of the enclosure 106). Clockwise rotation of the cylinder arrangement causes the helical spring 202 to rotate clockwise about the longitudinal axis, forcing the distal end 202a through the curved slot 246 and out of the hole 110, thereby increasing the length of the helical spring 202 from the initial compressed length (FIG. 3A), towards the initial deployed length (FIG. 1B), and ultimately towards the maximum deployed length (FIG. 1C) of the deployed state. As the distal end 202a is forced through the curved slot 246 and out of the hole 110, the helical spring 202 unwinds from around the exterior surface of the hollow inner cylinder 218. The clockwise rotation allows the helical spring 202 to advance (i.e., lengthen) under its own force, without the need to generate axial forces to push the helical spring 202 into the oral cavity and/or the upper airway.

Similarly, when moving from the deployed state to the retracted state, actuation of the electric motor 212, by the control unit 204, causes the cylinder arrangement to rotate in a counter clockwise direction of rotation. Counter clockwise rotation of the cylinder arrangement causes the helical spring 202 to rotate counter clockwise about the longitudinal axis, pulling the distal end 202a towards the hole 110 and the curved slot 246, and decreasing the length of the helical spring 202 from the deployed length, towards the fully compressed and initial length of the retracted state (FIG. 3A). Accordingly, counter clockwise rotation of the helical spring 202 causes the helical spring 202 to wind around the exterior surface of the hollow inner cylinder 218, within the annular space 226.

In a non-limiting implementation, the electro-mechanical drive arrangement 210 is configured to continually rotate the helical spring 202, clockwise, subsequent to the helical spring 202 reaching the deployed state, and ultimately subsequent to the helical spring 202 reaching the maximum deployed length. The rate of rotation of the helical spring 202 in the clockwise direction of rotation subsequent to reaching the maximum deployed length is preferably in the range of 0.1-1 rotations per minute. Accordingly, once fully deployed, the helical spring 202 is moved, via rotation, against different contact points of tissue inside the oral cavity and/or the upper airway, in a rhythmic type motion, or other type of motion which the electric motor 212 can be programmed to execute. As a result, the distal end 202a constantly changes the regions of contact between the helical spring 202 and the tissue in oral cavity and/or the upper airway. This reduces the risk of the development of pressure sores due to increased pressure on the region of contact tissue and lower than atmospheric pressure in the upper airway due to the inhalation of air by the user. Additionally, such continual rotation and movement increases the efficacy of the intra-oral device 10 by repositioning the elastic support member 202 to contact the region of contact tissue in the event that the elastic support member 202 is displaced by the tongue or other muscles in the oral cavity.

As mentioned above, the control unit 204 actuates the electric motor 212 to drive the retraction and deployment mechanism 216. The actuation by the control unit 204 may be based on input received from a sensor arrangement 230 which may include a variety of sensors for providing information and data relevant to the user, including, but not limited to, air pressure sensors, air flow sensors, temperature sensors, optical heart rate sensors, optical pulse oximetry sensors, electromyography (EMG) sensors, force sensors, audio sensors, motion sensors, and humidity sensors. Such sensors may be implemented as transducers, and are preferably in fluid flow communication with the air in the oral cavity of the user, or suitably installed within the enclosure 106 so as to properly generate associated electrical signals. Such sensors may be used to gather data and assess the physiological state of the user, by, for example, determining parameters for evaluating, such as, for example, respiration status, onset of apnea and hypopnea, blood oxygenation, heart rate, gross body motions, bruxism, snoring and sleep/wake status.

The sensors of the sensor arrangement 230 provide electrical signals to the control unit 204, which are preferably digitized by the ADC 207 before being processed by the processor 205. The processor 205 preferably runs real-time program code, such as, for example, firmware, which allows for real-time operation of the components of the intra-oral device 10. Accordingly, the control unit 204 may actuate the electro-mechanical drive arrangement 210 to deploy the helical spring 202 at a prescribed rate of deployment, retract the helical spring 202 at a prescribed rate of retraction, and continually rotate the helical spring 202 at a prescribed rate subsequent to movement to the deployed state. In addition, data collected from the sensors of the sensors arrangement 230 may be stored in the storage medium 208, or another memory, such as, for example, a non-volatile memory, coupled to the processor 205, for analysis. The same sensor data may be used to modulate the functioning of the real-time program code, in ways that may increase the efficacy of the treatment. For example, such modulation may result in an increase in the length of the deployed elastic support member 202 if apneic events are still detected while the elastic support member 202 is already deployed, or may prevent the deployment of the elastic support member 202 if the sensor data is interpreted as indicating that the user is still awake. Additional conditions for such modulations will be presented in further detail in subsequent sections of the present disclosure.

The sensor arrangement 230 may also include an integrity sensor for measuring the integrity of the elastic support member 202. Accordingly, if the integrity of the elastic support member 202 is determined to be compromised, due to malfunction or damage, based on received signals from the integrity sensor, the control unit 204 may be configured to refrain from actuating the electro-mechanical drive arrangement 210 to move the elastic support member 202, to either of the deployed or retracted states to avoid causing damage to the tissue in the oral cavity and/or upper airway, and to avoid further damaging the intraoral device 10.

As mentioned above, the intra-oral device 10 may be removably coupled to a bedside unit 300, connected to a mains voltage power supply that includes a charging arrangement 302 for recharging the rechargeable power supply 206 via the metallic screws 108. The removable coupling of the intra-oral device 10 to the bedside unit 300 may be via receiving interface (not shown) in the bedside unit, such as, for example, a docking station.

The intra-oral device 10 may be configured, via the control unit 204, to deploy the helical spring 202 to the maximum deployed length when the intra-oral device 10 is docked in the docking station of the bedside unit 300. Such deployment allows for manual or automatic cleaning and disinfection of the helical spring 202 during docking. Additionally, integrity validation of the components and sub-components of the intra-oral device 10 may be performed during docking. Upon completion of cleaning, disinfection, and integrity verification, the helical spring 202 moves to the retracted state.

Additionally, the bedside unit 300 preferably includes a control unit 304 and a user interface (UI) 312. As shown in FIG. 6, the control unit 304 includes at least one processor 305 coupled to a storage medium 308 such as a memory or the like. The processor 305 can be any number of computer processors, including, but not limited to, a microcontroller, a microprocessor, an ASIC, a DSP, and a state machine. Such processors include, or may be in communication with computer readable media, which stores program code or instruction sets that, when executed by the processor, cause the processor to perform actions. Types of computer readable media include, but are not limited to, electronic, optical, magnetic, or other storage or transmission devices capable of providing a processor with computer readable instructions.

In a non-limiting implementation, both of the control units 204 and 304 are coupled to respective communication units, 209 and 309, allowing for the intra-oral device 10 to transmit recorded physiological data and parameters recorded via the sensor arrangement 230 to the bedside unit 300. The communication between the communication units 209 and 309 may be via any suitable short range communication paradigm known in the art. Accordingly, the control unit 204 is configured to actuate the communication unit 209 to transmit such data to the communication unit 309. The data received by the communication unit 309 may be subsequently stored in the storage medium 308, or another memory, such as, for example, a non-volatile memory, coupled to the processor 305, for analysis. Additionally, the control unit 304 may be configured to actuate, via instructions transmitted by the communication unit 309 and received. by the communication unit 209, the electro-mechanical drive arrangement 210 to move the helical spring 202 between the retracted and deployed states or any position in between these states The UI 312 is permanently couple(to the control unit 304, and may also couple to the control unit 204 when the intra-oral device 10 is docked with the bedside unit 300. As such, the UI 312 allows the user to retrieve data stored in a memory of the intra-oral device 10 or the bedside unit 300, such as, for example, the storage mediums 208 and 308. The bedside unit 300 may further include input and output ports for connecting the bedside unit 300 to a computing device, such as, for example, a laptop or desktop computer, or a personal communication computing device, such as, for example, a tablet or smartphone. The UI 312 may be implemented as any suitable interface platform, such as, for example, a touchscreen or the like.

In addition to the above, the UI 312 also allows the user to select different modes of operation of the intra-oral device 10 when in use. In order to better understand the operation of the intra-oral device 10, several different deployment modes are presented herein. As should be understood, the deployment modes as will be described herein represent non-limiting examples of possible deployment scenarios of the intra-oral device 10, and that other deployment scenarios of the intra-oral device 10 may be possible.

One non-limiting exemplary deployment mode is hereinafter referred to as "Timed Mode" In Time Mode, the control unit 204 actuates the electro-mechanical drive arrangement 210 to begin moving the helical spring 202 from the retracted state to the deployed state after a predetermined period of time elapses from activation of the intra-oral device 10. The predetermined period of time is preferably set by the user via the UI 312 when the intra-oral device 10 is docked with the bedside unit 300. Accordingly, the intra-oral device 10 becomes active, or is activated, upon decoupling of the intra-oral device 10 from the bedside unit 300. The user preferably sets the predetermined time to allow enough time for the user to fall asleep before movement of the helical spring 202 begins. Accordingly, the user secures the intra-oral device 10 to the mouth with the helical spring 202 in the retracted state, via the base member 102, and falls asleep. Once predetermined time has elapsed, the helical spring 202 moves from the retracted state to the deployed state.

Another non-limiting deployment mode is hereinafter referred to as "Sleep Mode". In Sleep Mode, the control unit 204 analyzes received signals from the sensor arrangement 230, via. the ADC module 207 and the processor 205 as discussed above. Such signals may provide an indication of the presence of one or more physiological parameters gathered from within the oral cavity, including, but not limited to, respiration airflow, temperature, humidity, heart rate, oximetry and EMG of the tongue or other muscles in the oral cavity. The analysis of the received signals by the control unit 204 allows the control unit 204 to make a determination if the user is asleep or awake. Upon the determination (i.e., detection), by the control unit 204, of the onset of sleep or any other predetermined sleep stage or event, the control unit 204 actuates the electro-mechanical drive arrangement 210 to begin moving the helical spring 202 from the retracted state to the deployed state.

Another non-limiting deployment mode is hereinafter referred to as "Apnea Mode". Similar to as in Sleep Mode, in Apnea Mode, the control unit 204 analyzes received signals from the sensor arrangement 230, via the ADC module 207 and the processor 205 as discussed above. Such signals may provide an indication as to whether the user is experiencing respiratory events such as snoring, hypopneas or apneas. The analysis of the received signals by the control unit 204 allows the control unit 204 to make a determination if the user is experiencing such respiratory events. Upon the determination (i.e., detection), by the control unit 204, of the onset of such respiratory events, the control unit 204 actuates the electro-mechanical drive arrangement 210 to begin moving the helical spring 202 from the retracted state to the deployed state.

Timed Mode, Sleep Mode, and Apnea Mode share the common condition that the intra-oral device 10 is positioned in the mouth of the user, via the base member 102, with the helical spring 202 in the retracted state. Furthermore, in the above described modes, the movement of the helical spring 202 from the retracted state to the deployed state occurs subsequent to the user falling asleep. As such, insertion of the intra-oral device 10 in the mouth with the helical spring 202 in the retracted state alleviates the gag reflex upon insertion, and reduces the negative psychological effects associated with insertion of the intra-oral device 10 in the mouth.

As previously discussed, while the helical spring 202 is in the deployed state, during the three above mentioned modes of use, the electro-mechanical drive arrangement 210 may be configured to continually rotate the helical spring 202 to reduce the risk of the development of pressure sores in the oral cavity and/or the upper airway. Additionally, the control unit 204 may be configured to actuate the electro-mechanical drive arrangement 210 to adjust the length of the helical spring 202, while maintaining the helical spring 202 in the deployed state, based on the severity of respiratory disturbances measured from signals received from the sensor arrangement 230. Accordingly, the control unit 204 may actuate the electro-mechanical drive arrangement 210 to lengthen the helical spring 202 when more respiratory disturbances are measured, and shorten the helical spring 202 when fewer respiratory disturbances are measured. In other words, while in the deployed state, the control unit 204 may actuate the electro-mechanical drive arrangement 210 to vary the length of the helical spring 202 towards the maximum deployed length when more respiratory disturbances are measured, and towards the initial deployed length when fewer respiratory disturbances are measured.

As the user nears waking, the helical spring 202 moves from the deployed state to the retracted state. Such movement may he accomplished in various ways. In order to better understand the operation of the intra-oral device 10, several different retraction modes are presented herein. As should be understood, the retraction modes as will be described herein represent non-limiting examples of possible retraction scenarios of the intra-oral device 10, and that other retraction scenarios of the intra-oral device 10 may be possible.

One retraction mode follows a methodology similar to that of Timed Mode, described above. In such a retraction mode, a time may be set, via the UI 312 when the intra-oral device 10 is docked with the bedside unit 300, at which the control unit 204 actuates the electro-mechanical drive arrangement 210 to move the helical spring 202 from the deployed state to the retracted state. Alternatively, the intra-oral device 10 may receive the time as input, via the communication unit 209, from an external alarm clock, or via an alarm clock embedded as part of the bedside unit 300. Alternatively, the intra-oral device 10 may receive the time as input, via the communication unit 209 or the control unit 204, from a wireless or wired remote control. Preferably, the control unit 204 actuates the electro-mechanical drive arrangement 210 to move the helical spring 202 from the deployed state to the retracted state slightly before the set time, allowing enough time for retraction before the user awakens. Accordingly, upon waking from the sleep, the user may remove the intra-oral device 10 from the mouth with the helical spring 202 mostly or fully retracted.

Another retraction mode follows a methodology similar to that of Sleep Mode and Apnea Mode, described above. In such a retraction mode, the control unit 204 analyzes received signals from the sensor arrangement 230, via the ADC module 207 and the processor 205 as discussed above. Such signals may provide an indication as to whether the user is experiencing signs of waking, such as, for example, EMG, increased heart rate variability, and increased body motion. The analysis of the received signals by the control unit 204 allows the control unit 204 to make a determination if the user is experiencing such signs of waking. Upon the determination (i.e., detection), by the control unit 204, of the waking, the control unit 204 actuates the electro-mechanical drive arrangement 210 to begin moving the helical spring 202 from the deployed state to the retracted state.

Additionally, the control unit 204 may analyze received signals from the sensor arrangement 230 over a period of several nights, in order to make a determination or prediction of the time of waking of the user. Such a prediction may be made by implementing, via the processor 205, algorithms such as, for example, supervised learning algorithms, unsupervised learning algorithms, and pattern recognition algorithms. Accordingly, the control unit 204 is able to actuate the electro-mechanical drive arrangement 210 to begin moving the helical spring 202 from the deployed state to the retracted state at the predicted time of waking.

The above described retraction modes may be operatively used with any of the above mentioned deployment modes (e.g., Timed Mode, Sleep Mode, and Apnea Mode). It is noted that in addition to the retraction modes described above, the user may remove the intra-oral device 10 from the mouth when the helical spring 202 is in the deployed state. The shape of the helical spring 202, as well as the material used to form the helical spring 202, allows the helical spring 202 to be deformed into a generally straight wire when the intra-oral device 10 is removed from the mouth when the, helical spring 202 is in the deployed state. This prevents the helical spring 202 from becoming caught on, or stuck in, oral structures within the oral cavity and upper airway, such as, for example, the uvula. Subsequent to removal from the mouth of the user, the generally straight wire reforms into the helical spring 202 shape.

Although the intra-oral device 10 as described thus far has pertained to all of the components of the electro-mechanical assembly 200 housed within the enclosure 106, other embodiments are possible in which several of the components of the electro-mechanical assembly 200 are positioned outside of the enclosure 106, and outside of the mouth of the user. For example, such embodiments may include positioning some of the sensors of the sensor arrangement 230 outside of the mouth of the user. Additionally, actuation of the electro-mechanical drive arrangement 210 may be provided by a control unit external to the mouth of the user, such as, for example, the control unit 304 of the bedside unit 300. Additionally, mechanical components of the electro-mechanical drive arrangement 210 may be positioned outside of the mouth of the user as well. In such embodiments, the components located outside of the mouth of the user are preferably electrically and/or mechanically coupled to the components located within the enclosure 106.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. As used herein, the singular form "a", "an" and "the" include plural references unless the context clearly dictates otherwise.

The word "exemplary" is used herein to mean "serving as an example, instance or illustration". Any embodiment or implementation described as "exemplary" is not necessarily to be construed as preferred or advantageous over other embodiments and/or to exclude the incorporation of features from other embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A device for reducing breathing obstructions of a user, comprising:
   a base member for removably coupling to the upper or lower jaw of the user;
   an elastic support member operatively coupled to the base member, the elastic support member including at least one contact surface for contacting at least one region of tissue, the elastic support member movable between a retracted state, in which the at least one contact surface is configured to be spatially separated from the at least one region of tissue, and a deployed state, in which at least a portion of the elastic support member is extended, such that the at least one contact surface is configured to contact the at least one region of tissue to prevent at least partial collapse of at least a section of the upper airway of the user;
   an electro-mechanical drive arrangement in mechanical driving relationship with the elastic support member; and
   a control unit associated with the electro-mechanical drive arrangement, the control unit configured for actuating the electro-mechanical drive arrangement to move the elastic support member between the retracted and deployed states.

2. The device of claim 1, wherein when the elastic support member is in the retracted state, the elastic support member assumes an initial volume, and when the elastic support member is in the deployed state, the elastic support member is operative to assume a range of volumes between an initial deployed volume and a maximum deployed volume.

3. The device of claim 1, wherein when the elastic support member is in the retracted state, the elastic support member assumes an initial length, and when the elastic support member is in the deployed state, the elastic support member is operative to assume a range of lengths between an initial deployed length and a maximum deployed length.

4. The device of claim 1, wherein when the elastic support member is in the retracted state, the majority of the elastic support member is configured to be retained in a compressed state within the mouth of the user.

5. The device of claim 1, wherein movement between the retracted state to the deployed state is induced by rotation of the elastic support member about a longitudinal axis of the elastic support member.

6. The device of claim 1, wherein the elastic support member includes a helical spring.

7. The device of claim 1, wherein the at least one region of tissue includes a plurality of regions of tissue, and subsequent to movement of the elastic support member to the deployed state, the elastic support member is operative to maintain continuous movement to reposition the at least one contact surface to contact any of the plurality of regions of tissue.

8. The device of claim 1, wherein the electro-mechanical drive arrangement includes a cylinder arrangement comprising an inner cylinder including an exterior surface, and a hollow outer cylinder including an interior surface defining an interior volume, at least a portion of the inner cylinder being positioned within the interior volume of the hollow outer cylinder thereby defining an annular space between the exterior surface of the inner cylinder and the interior surface of the hollow outer cylinder.

9. The device of claim 8, wherein the majority of the elastic support member is retained within the annular space when the elastic support member is in the retracted state.

10. The device of claim 1, further comprising one or more sensors associated with the control unit, the one or more sensors selected from the group consisting of: a pressure senor, a temperature sensor, a humidity sensor, a blood pressure sensor, an audio sensor, a vibration sensor, a tissue contact sensor, an optical peripheral capillary oxygen saturation sensor, an electromyography sensor, and a force sensor.

11. The device of claim 10, wherein each of the one or more sensors is configured to provide signals to the control unit, and the control unit is configured to actuate or refrain from actuating the electro-mechanical drive arrangement to move the elastic support member according to at least one rule.

12. The device of claim 1, wherein the base member includes an arcuate perimeter surface that includes first and second branches.

13. The device of claim 12, wherein the base member further includes a band having first and second ends, the first end fixedly coupled to the first branch and the second end fixedly coupled to the second branch, such that the band extends laterally across the base member, and the elastic support member is fixedly coupled to at least a portion of the band.

14. The device of claim 1, wherein the at least one region of tissue includes at least a portion of the pharynx.

15. The device of claim 1, wherein when the elastic support member is in the deployed state, the elastic support member is configured to provide a force profile to the at least one region of tissue that includes a radial component of force.

16. The device of claim 1, wherein the base member includes a plurality of anchoring members, each respective anchoring member for removably attaching to a respective tooth or tooth pair of the user.

17. The device of claim 16, wherein each of the anchoring members includes a mold of the respective tooth or tooth pair.

18. A device for reducing breathing obstructions of a user, comprising:
   a base member for removably coupling to the upper or lower jaw of the user;
   an elastic support member operatively coupled to the base member, the elastic support member including at least one contact surface for contacting a region of tissue, the elastic support member operative to assume a range of volumes between an initial volume, in which the at least one contact surface is configured to be spatially separated from the region of tissue, and a second volume, in which at least a portion of the elastic support member is extended, such that the at least one contact surface is configured to contact the region of tissue and the elastic support member is configured to provide a force profile to the region of tissue to prevent at least partial collapse of at least a section of the upper airway of the user, the initial volume being at least half of the second volume;

an electro-mechanical drive arrangement in mechanical driving relationship with the elastic support member; and a control unit associated with the electro-mechanical drive arrangement, the control unit configured for actuating the electro-mechanical drive arrangement to adjust the volume of the elastic support member.

19. A device for reducing breathing obstructions of a user, comprising:

a base member for removably coupling to the upper or lower jaw of the user;

an elastic support member operatively coupled to the base member, the elastic support member including at least one contact surface for contacting a region of tissue, the elastic support member operative to assume a range of lengths between an initial length, in which the at least one contact surface is configured to be spatially separated from the region of tissue, and a second length, in which at least a portion of the elastic support member is extended, such that the at least one contact surface is configured to contact the region of tissue and the elastic support member is configured to provide a force profile to the region of tissue to prevent at least partial collapse of at least a section of the upper airway of the user;

an electro-mechanical drive arrangement in mechanical driving relationship with the elastic support member; and a control unit associated with the electro-mechanical drive arrangement, the control unit configured for actuating the electro-mechanical drive arrangement to adjust the length of the elastic support member.

* * * * *